(12) United States Patent
Noda et al.

(10) Patent No.: US 7,178,382 B2
(45) Date of Patent: Feb. 20, 2007

(54) STRUCTURE OF GAS SENSOR DESIGNED TO REDUCE MECHANICAL DAMAGE TO SENSOR ELEMENT

(75) Inventors: Hirofumi Noda, Kariya (JP); Takashi Kojima, Kasugai (JP)

(73) Assignee: Denso Corporation, Kariya (JP)

( * ) Notice: Subject to any disclaimer, the term of this patent is extended or adjusted under 35 U.S.C. 154(b) by 111 days.

(21) Appl. No.: 11/019,724

(22) Filed: Dec. 23, 2004

(65) Prior Publication Data

US 2005/0138989 A1 Jun. 30, 2005

(30) Foreign Application Priority Data

Dec. 24, 2003 (JP) ............... 2003-427260

(51) Int. Cl.
*G01N 7/00* (2006.01)
(52) U.S. Cl. ...................... 73/31.05; 73/23.2
(58) Field of Classification Search .............. 73/31.05, 73/23.2, 23.32
See application file for complete search history.

(56) References Cited

U.S. PATENT DOCUMENTS

| 4,784,743 A | * | 11/1988 | Iino et al. ................ 204/425 |
| 5,762,771 A | * | 6/1998 | Yamada et al. ............ 204/428 |
| 6,214,186 B1 | * | 4/2001 | Watanabe et al. .......... 204/428 |
| 6,708,551 B2 | * | 3/2004 | Kojima ..................... 73/31.05 |
| 6,749,732 B2 | * | 6/2004 | Nakagawa et al. ......... 204/428 |
| 6,948,353 B2 | * | 9/2005 | Toguchi et al. ............ 73/23.31 |
| 2003/0024300 A1 | * | 2/2003 | Kojima ..................... 73/31.05 |

FOREIGN PATENT DOCUMENTS

| JP | 2002-174622 | 6/2002 |
| JP | 2003-294682 | 10/2003 |
| JP | 2003-294684 | 10/2003 |

* cited by examiner

*Primary Examiner*—Hezron Williams
*Assistant Examiner*—Rodney Frank
(74) *Attorney, Agent, or Firm*—Nixon & Vanderhye, P.C.

(57) ABSTRACT

An improved structure of a gas sensor designed to withstand physical impact which may result in damage such as cracks to a sensor element built in the gas sensor. Specifically, the gas sensor includes a buffer provided by a clearance between an air cover a porcelain insulator. The clearance is in a range of 1 to 2.5 mm at a minimum. The gas sensor may alternatively have a harder portion in the air cover which has a Vickers hardness of 200 to 400. The gas sensor may alternatively have a rigidity enhancer in the air cover which works to provides an increased rigidity to the air cover.

13 Claims, 9 Drawing Sheets

STRUCTURE OF GAS SENSOR DESIGNED TO REDUCE MECHANICAL DAMAGE TO SENSOR ELEMENT

CROSS REFERENCE TO RELATED DOCUMENT

The present application claims the benefit of Japanese Patent Application No. 2003-427260 filed on Dec. 24, 2003, the disclosure of which is incorporated herein by reference.

BACKGROUND OF THE INVENTION

1. Technical Field of the Invention

The present invention relates generally to a gas sensor which may be installed in an exhaust system of an internal combustion engine for burning control thereof, and more particularly to an improved structure of such a gas sensor designed to reduce mechanical damage such as cracks to a sensor element which arises from a physical impact acting on the gas sensor.

2. Background Art

Some modern air-fuel ratio controls for automotive engines are equipped with a gas senor of the type, as taught in Japanese Patent First Publication No. 2002-174622, which is installed upstream of an exhaust pipe of the engine.

In recent years, regulations on exhaust emissions from automotive vehicles have been tightened, and with it there have been increased cases where the gas sensor is installed downstream of a catalytic converter of an exhaust system of automotive engines to monitor the condition of exhaust gas emitted from the catalytic converter.

However, when installed downstream of the exhaust pipe of the automotive engines, the gas sensor is usually exposed from the bottom of the vehicle body, thus resulting in an increased possibility of being subjected to physical impact such as hits from stones. When the stones hit an outer cover of the gas sensor, it may cause the cover to be deformed, which, in the worst case, results in cracks in the sensor element built in the gas sensor.

In order to withstand the impact, the cover of the gas sensor may be increased in thickness, but it results in an increased weight of the gas sensor and also difficulty in shaping the cover.

SUMMARY OF THE INVENTION

It is therefore a principal object of the invention to avoid the disadvantages of the prior art.

It is another object of the invention to provide an improved structure of a gas sensor which is designed to reduce physical damage such as cracks to a sensor element built in the gas sensor.

According to the first aspect of the invention, there is provided a gas sensor which comprise: (a) a hollow cylindrical housing having a top end portion and a base end portion; (b) a first porcelain insulator disposed in the housing; (c) a sensor element having a length made up of a sensing portion and a base portion, the sensor element being retained in the housing through the first porcelain insulator; (d) a cylindrical gas cover affixed to the top end portion of the housing to cover the sensing portion of the sensor element; (e) a second porcelain insulator in which the base portion of the sensing element is disposed; (f) a cylindrical air cover covering the second porcelain insulator, the air cover having a length made up of a small-diameter portion, a large-diameter portion, a shoulder formed between the small-diameter portion and the large-diameter portion, and a press-fit end continuing from the large-diameter portion, the small-diameter portion being crimped to retain an elastic insulator therein, the press-fit end being press fit on the base end portion of the housing to make a joint of the air cover to the housing, the large-diameter portion having an inner side wall facing an outer side wall of the second porcelain insulator; and (g) a buffer provided by a clearance between the inner side wall of the large-diameter portion of the air cover and the outer side wall of the second porcelain insulator. The clearance lies in a range of 1 to 2.5 mm at a minimum.

A typical one of factors attributed to cracks in the sensor element is an external impact causing the air cover to be deformed and hit on the second porcelain insulator. The buffer provided by the clearance lying within the above range works to absorb such impact completely or partially to reduce physical shock on the sensor element. This results in a decreased possibility of cracks in the sensor element.

In the preferred mode of the invention, the buffer extends over the whole of the inner side wall of the large-diameter portion of the air cover in a lengthwise direction of the air cover.

The cover has a wall thickness of 0.3 to 0.8 mm. When the wall thickness is less than 0.3 mm, it leads to a concern about mechanical breakage of the air cover during forming it. When the wall thickness is more than 0.8 mm, it results in a difficulty in shaping the air cover and also an increased overall weight of the gas sensor.

The air cover is made of an austenitic stainless steel to provide for erosion resistance.

According to the second aspect of the invention, there is provided a gas sensor which comprises: (a) a hollow cylindrical housing having a top end portion and a base end portion; (b) a first porcelain insulator disposed in the housing; (c) a sensor element having a length made up of a sensing portion and a base portion, the sensor element being retained in the housing through the first porcelain insulator; (d) a cylindrical gas cover affixed to the top end portion of the housing to cover the sensing portion of the sensor element; (e) a second porcelain insulator in which the base portion of the sensing element is disposed; and (f) a cylindrical air cover covering the second porcelain insulator. The air cover has a harder portion whose Vickers hardness lies within a range of 200 to 400. Specifically, the air cover has increased rigidity to withstand physical impact, thus resulting in a decreased possibility of cracks in the sensor element.

In the preferred mode of the invention, the air cover has a length made up of a small-diameter portion, a large-diameter portion, a shoulder formed between the small-diameter portion and the large-diameter portion, and a press-fit end continuing from the large-diameter portion. The small-diameter portion is crimped to retain an elastic insulator therein. The large-diameter portion has an inner wall facing the second porcelain insulator. The press-fit end is press fit on the base end portion of the housing to make a joint of the air cover to the housing. The press-fit end has a Vickers hardness of 140 to 200. This is because materials which have a Vickers hardness of less than 140 and yet withstand erosion are unavailable, and when the Vickers hardness is more than 200, it results in a difficulty in fitting the air cover on the housing.

The air cover may be subjected to work hardening to achieve a desired hardness.

According to the third aspect of the invention, there is provided a gas sensor which comprises: (a) a hollow cylindrical housing having a top end portion and a base end portion; (b) a first porcelain insulator disposed in the housing; (c) a sensor element having a length made up of a sensing portion and a base portion, the sensor element being retained in the housing through the first porcelain insulator; (d) a cylindrical gas cover affixed to the top end portion of the housing to cover the sensing portion of the sensor element; (e) a second porcelain insulator in which the base portion of the sensing element is disposed; (f) a cylindrical air cover covering the second porcelain insulator; and (g) a rigidity enhancer provided in the air cover which provides an increased rigidity to the air cover, thereby resulting in a decreased possibility of cracks in the gas sensor.

In the preferred mode of the invention, the rigidity enhance is implemented by protrusions and recesses each of which is disposed between adjacent two of the protrusions. The protrusions and recesses extend in an axial direction of the gas sensor.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
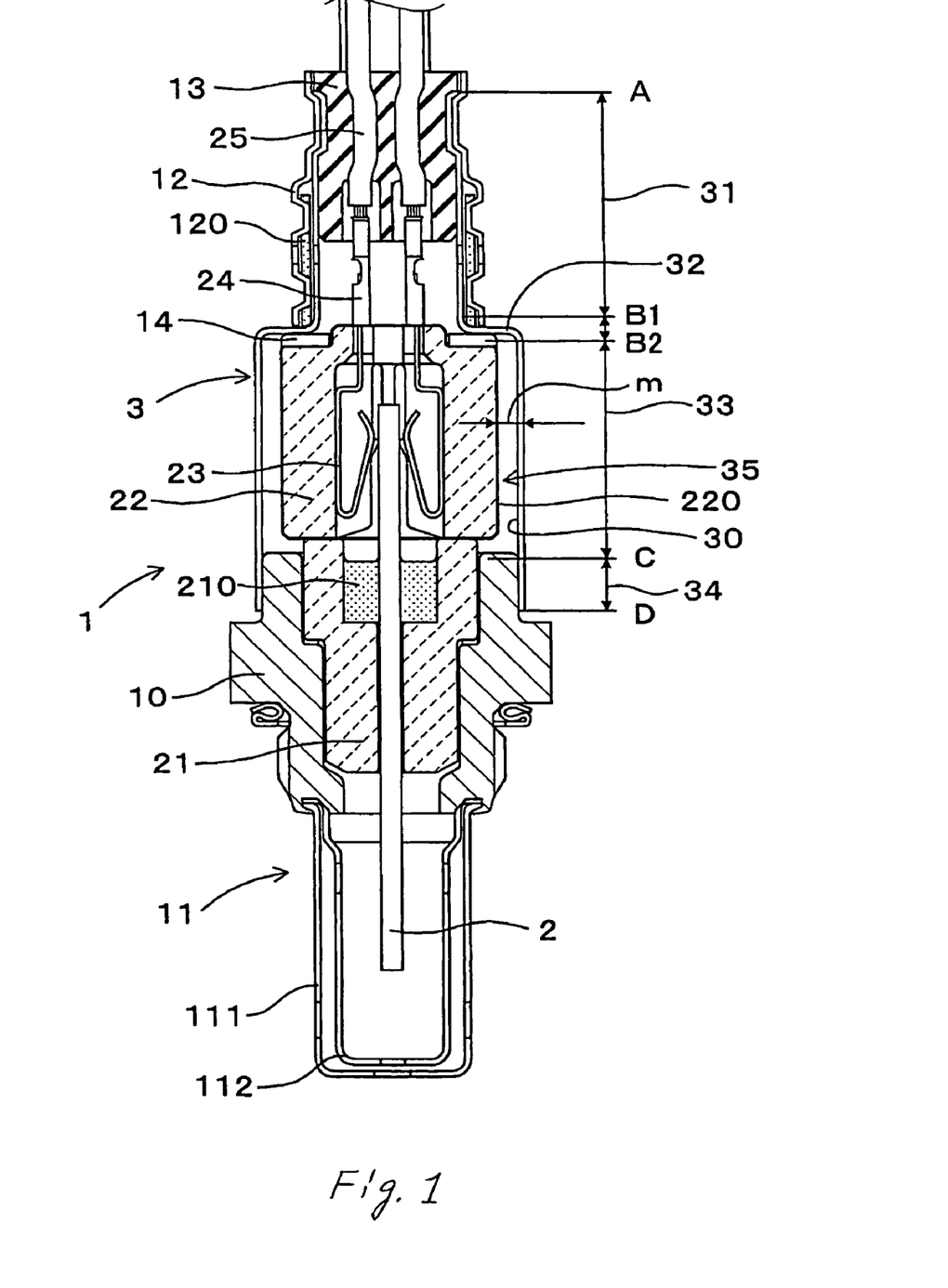
FIG. 1 is a longitudinal sectional view which shows a gas sensor according to the first embodiment of the invention.

Referring to the drawings, wherein like reference numbers refer to like parts in several views, particularly to FIG. 1, there is shown a gas sensor 1 according to the first embodiment of the invention which may be employed in an air-fuel ratio control system for automotive vehicles to measure the concentration of a component such as $O_2$, NOx, CO, or HC contained in exhaust gasses of the engine The gas sensor 1 may also be of a limited current type or a concentration dependent electromotive force type which is well known in the art as measuring the concentration of oxygen.

The gas sensor 1 generally includes a sensor element 2, a lower porcelain insulator 21, an upper porcelain insulator 22, a hollow cylindrical housing 10, a cylindrical protective cover assembly 11, and a cylindrical air cover 3. The sensor element 2 may be made of a laminated solid electrolyte body or cup-shaped solid electrolyte body and have a heater embedded therein or affixed thereto to heat the sensor element 2 up to an activation temperature at which the sensor element 2 will be sensitive to a target gas correctly. The structure of such a type of sensor element is well known in the art and not an essential part of this invention. Explanation thereof in detail will be omitted here.

The lower porcelain insulator 21 is fitted within the housing 10 and holds therein the sensor element 2 through a glass sealing member 210. The upper porcelain insulator 22 is mounted on the lower porcelain insulator 21 and surrounds a base portion of the sensor element 2. The air cover 3 is installed at an end thereof on the housing 10 and surrounds the upper porcelain insulator 22.

The air cover 3 is made up of a small-diameter portion 31, a shoulder 32, a large-diameter portion 33, and a press-fit end 34. The small-diameter portion 32 is crimped to retain therein an insulating holder 13 tightly. The insulating holder 13 may be made of an elastic member such as rubber. The shoulder 32 extends from an end of the small-diameter portion 31 outwardly. The large-diameter portion 32 has an inner peripheral wall 30 face the upper porcelain insulator 22. The press-fit end 34 is press-fit on a base end of the housing 10 to make a mechanical joint of the air cover 3 to the housing 10.

The inner peripheral wall 30 of the large-diameter portion 32, as described above, face the upper porcelain insulator 22 through a cylindrical clearance (i.e., an air gap) of 1 to 2.5 mm at a minimum. The clearance extends in an axial direction of the large-diameter portion 32 (i.e., the gas sensor 1) and surrounds the whole of an outer side periphery of the upper porcelain insulator 22. The clearance works as a buffer 35 to reduce mechanical shock due to impact on the large-diameter portion 32. The clearance may have a minimum of 1 to 2.5 mm at least partially between the inner peripheral wall 30 of the large-diameter portion 32 and the outer side periphery of the upper porcelain insulator 22.

The protective gas cover assembly 11 is made up of outer and inner covers 111 and 112 and installed in a top end of the housing 10 to define a gas chamber into which a gas to be measured is admitted through gas holes formed in the outer and inner covers 111 and 112. The protective gas cover assembly 11 may be replaced with a single-walled cup-shaped cover. The air cover 3 is, as described above, fitted on the base end of the housing 10 and exposed to the air during use of the gas sensor 1. An outer cover 12 is provided around the air cover 3 and staked or crimped to retain a cylindrical water-repellent filter 120 on the periphery of the air cover 3. The air cover 3 and the outer cover 12 have formed therein air vents through which air is admitted into the air cover 3.

The sensor element 2 is, as described above, disposed within the lower porcelain insulator 21 and fixed firmly by the glass sealing member 210 which forms a seal between the sensor element 2 and the porcelain insulator 21.

The sensor element 2 has a length made up of a sensing portion and a base portion. The sensing portion is exposed to the gas to be measured within the protective gas cover assembly 11. The base portion has formed thereon electrode pads (not shown) which are in electric contact with spring terminals 23 within the upper porcelain insulator 22. The spring terminals 23 are connected at ends thereof to connectors 24 (e.g., crimp contacts) joined to leads 25 for transmitting a sensor output to an external device and supplying electric power to a heater (not shown) embedded in the sensor element 2. This structure is not an essential part of this invention and known in the art, and explanation thereof in detail will be omitted here.

The insulating holder 13 made of an elastic member such as rubber is fitted in a base end portion of the air cover 3 to hold the leads 25 therein. The air cover 3 and the outer cover 12 are crimped or pressed inwardly to retain the insulating holder 13 tightly within the air cover 3.

Figure 3:
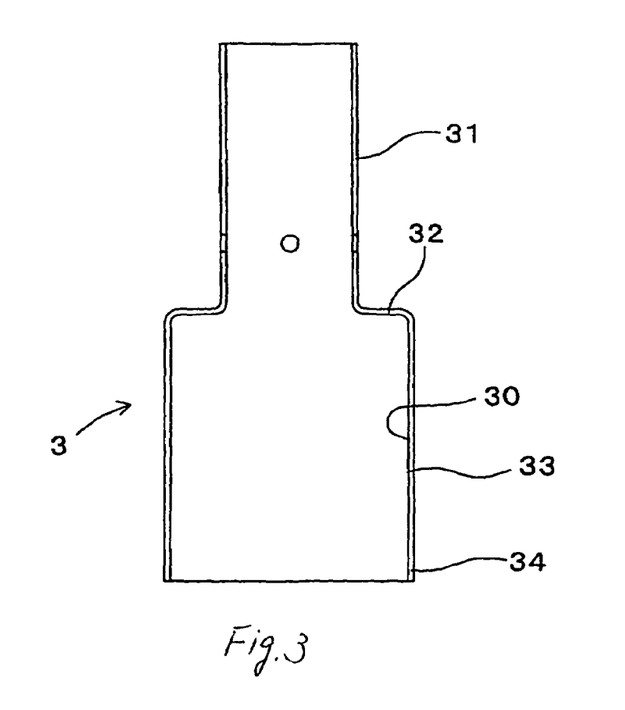
FIG. 3 is a longitudinal sectional view which shows an air cover of the gas sensor, as illustrated in FIG. 1.

The air cover 3 is formed by a 0.5 mm thick cylinder made of an austenitic stainless steel to provide for erosion resistance and has a substantially circular cross section. The wall thickness of the air cover 3 may lie within a range of 0.3 to 0.8 mm. When the wall thickness is less than 0.3 mm, it leads to a concern about mechanical breakage of the air cover 3 during forming it. When the wall thickness is more than 0.8 mm, it results in a difficulty in shaping the air cover 3 and also an increased overall weight of the gas sensor 1. The air cover 3 is, as described above, made up of the small-diameter portion 31, the shoulder 32, the large-diameter portion 33, and the press-fit end 34. The small-diameter portion 31 occupies, as clearly shown in FIG. 1, a section of an overall length of the air cover 3 between A and B1. The shoulder 32 occupies between B1 and B2. The large-diameter portion 33 occupies between B2 and C. The press-fit end 34 occupies between C and D. Before the small-diameter portion 31 is crimped, and the press-fit end 34 is pressed on the base end of the housing 11, each of the small-diameter portion 31 and the large-diameter portion 33 is, as clearly shown in FIG. 3, uniform in diameter over the length thereof.

A disc spring 14 is disposed between the shoulder 32 and an end of the upper porcelain insulator 22. The air cover 3 is press-fitted on the base end of the housing 10 to elastically deform the disc spring 14, thereby urging the upper porcelain insulator 22 into constant engagement with the lower porcelain insulator 21 to fix the location of the upper porcelain insulator 22 within the air cover 3 and to increase the degree of airtightness between the inner wall of the housing 10 and the lower porcelain insulator 21.

Figure 2:
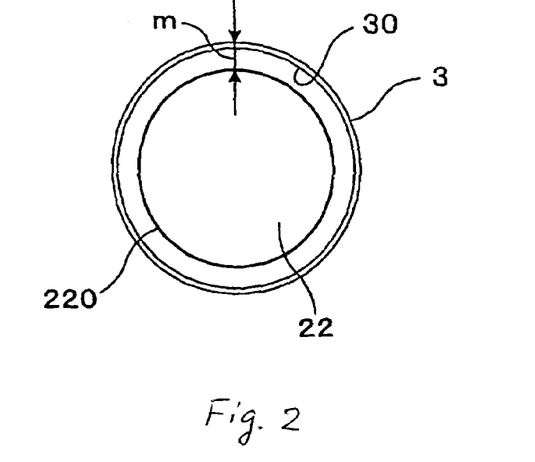
FIG. 2 is a transverse sectional view which shows an air cover and an upper porcelain insulator of the gas sensor, as illustrated in FIG. 1.

FIG. 2 is a transverse sectional view which shows the air cover 3. A minimum interval between the inner side wall 30 of the large-diameter portion 33 of the air cover 3 and the outer side wall 220 of the upper porcelain insulator 22 is expressed by m (also see FIG. 1). In this embodiment, the interval m is identical with the thickness of an overall clearance between the large-diameter portion 33 and the upper porcelain insulator 22 in the axial direction thereof which serves as the buffer 35. The interval m is within a range of 1 mm to 2.5 mm at a minimum.

A typical one of factors attributed to cracks in the sensor element 2 within the gas sensor 1 is an external impact causing the air cover 3 to be deformed and hit on the upper porcelain insulator 22. The buffer 35 provided between the air cover 3 and the upper porcelain insulator 22 works to absorb such impact completely or partially to reduce physical shock on the sensor element 2. This results in a decreased possibility of cracks in the sensor element 2.

Figure 4:
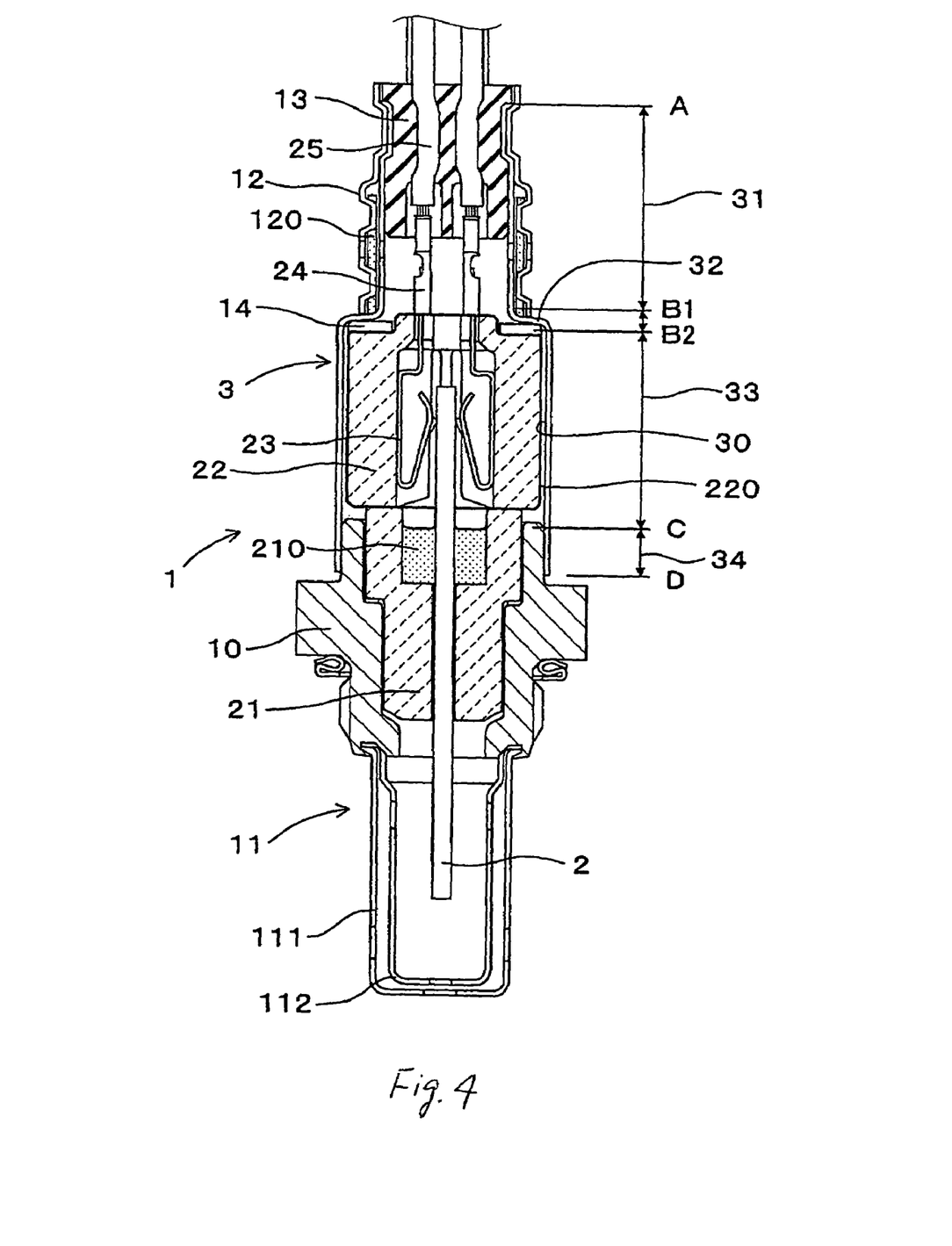
FIG. 4 is a longitudinal sectional view which shows a gas sensor according to the second embodiment of the invention.
Figure 5:
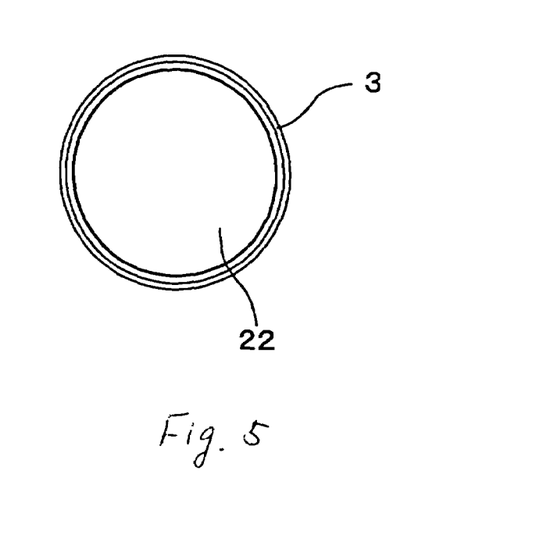
FIG. 5 is a transverse sectional view which shows an air cover and an upper porcelain insulator of the gas sensor, as illustrated in FIG. 4.
Figure 6:
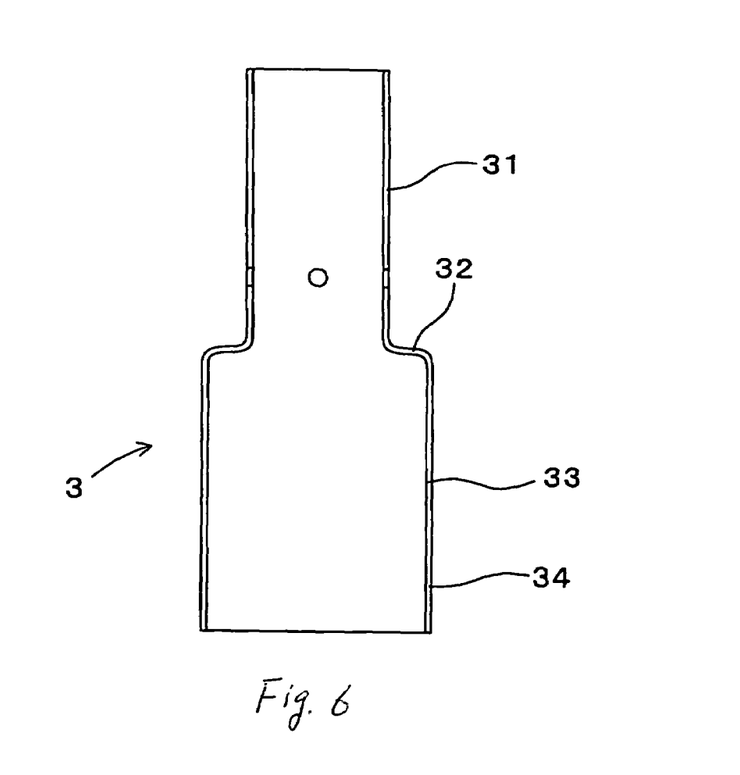
FIG. 6 is a longitudinal sectional view which shows an air cover of the gas sensor, as illustrated in FIG. 4.

FIGS. 4, 5, and 6 show the gas sensor 1 according to the second embodiment of the invention.

The gas sensor 1, like the one in FIG. 1, consists of the cylindrical housing 10, the sensor element 2 disposed within the housing 10 through the lower porcelain insulator 21, the protective cover assembly 11 installed in the top end of the housing 10, the cylindrical air cover 3 fitted on the base end of the housing 10, and the upper porcelain insulator 22 encompassing the base end portion of the sensor element 2 within the air cover 3.

The air cover 3 consists of the small-diameter portion 31, the shoulder 32, the large-diameter portion 33, and the press-fit end 34. The air cover 3 is made up of two parts in terms of hardness: one is a harder portion including the small-diameter portion 31, the shoulder 32, and the large-diameter portion 33 and the other is a softer portion including the press-fit end 34. The harder portion has a Vickers hardness of 200 to 400 (e.g., 250), while the softer portion has a Vickers hardness of 140 to 200 (e.g., 150) which facilitates ease of fitting of the press-fit end 34 on the housing 10. The harder portion may be provided by subjecting the air cover 3 to the so-called work hardening. The typical work hardening is a process of increasing the strength of metals through the phenomenon in which application of stress to the metal causes crystals thereof to slip, thereby resulting in an increased slip-resistance of slip planes of the crystals, and when the slip resistance of one of the slip planes exceeds an upper limit, the slip is transferred, in sequence, to other planes (plastic deformation).

A minimum distance or interval between the inner side wall 30 of the large-diameter portion 33 of the air cover 3 and the outer side wall 220 of the upper porcelain insulator 22 is less than 0.5 mm. Other arrangements are identical with those in the first embodiment, and explanation thereof in detail will be omitted here.

The harder portion of the air cover 3 works to withstand physical impact acting thereon, that is, is less susceptible to mechanical deformation, thereby resulting in a decreased possibility of hit of the air cover 3 with the upper porcelain insulator 22 leading to cracks in the sensor element 2.

The softer portion (i.e., the press-fit end 34) has a lower hardness and is easy to deform elastically, thus facilitating ease of fitting of the air cover 3 on the base end of the housing 10.

We researched cracks in the sensor element 2 of the gas sensor 1 in the first embodiment, as illustrated in FIG. 1, due to external physical impact acting on the gas sensor 1.

We prepared test samples of the gas sensor 1 which had a Vickers hardness of 150 over the whole of the air cover 3 and different intervals m of 0 mm to 2.5 mm (ten samples for each interval m), installed the test samples on a test model simulating a downstream portion of an exhaust pipe of automotive vehicles, and hurled stones at the test samples. This resulted many dents in the air cover 3 of each test sample.

Figure 7:
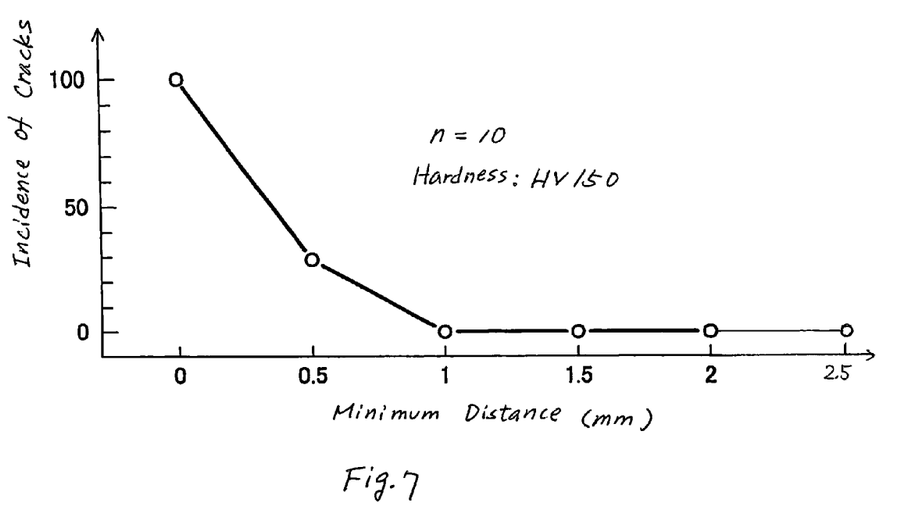
FIG. 7 is a graph which indicates the incidence of cracks in test samples of a gas sensor of the first embodiment in terms of an interval between an air cover and an upper porcelain insulator.

FIG. 7 is a graph which represents results of the above tests. The ordinate axis indicates the incidence of cracks in the test samples. The abscissa axis indicates the interval m between the air cover 3 and the upper porcelain insulator 22 of the test samples. The graph shows that there are no cracks occurring in the sensor element 2 when the interval m is 1 mm or more.

We also researched cracks in the sensor element 2 of the gas sensor 1 in the second embodiment, as illustrated in FIG. 4, due to external physical impact acting on the gas sensor 1.

Figure 8:
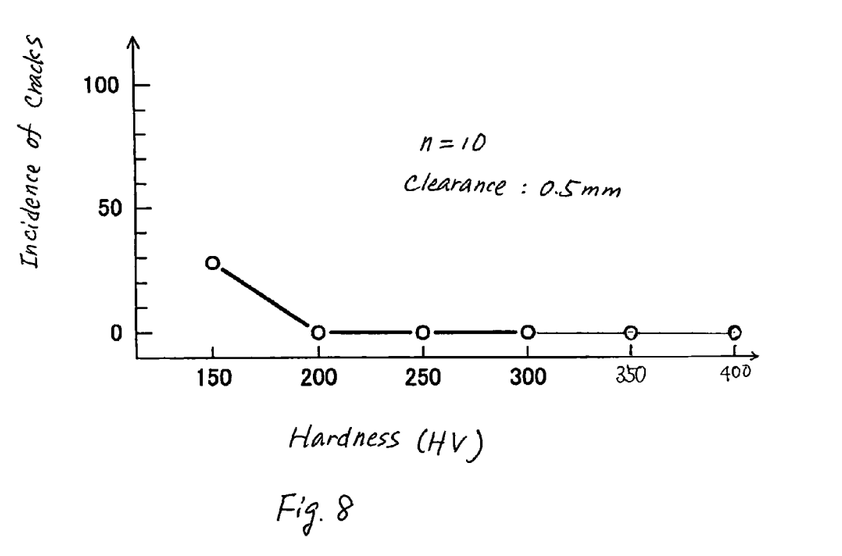
FIG. 8 is a graph which indicates the incidence of cracks in test samples of a gas sensor of the second embodiment in terms of hardness of an air cover.

We prepared test samples of the gas sensor 1 which had Vickers hardness of 150, 200, 250, 300, 350, and 400 in the harder portion (i.e., the small-diameter portion 31, the shoulder 32, and the large-diameter portion 33) of the air cover 3 (ten samples for each hardness) and observed cracks in the same manner as described above. FIG. 8 represents results of the tests and show that there are no cracks occurring in the sensor element 2 when the Vickers hardness is 200 or more.

Figure 9:
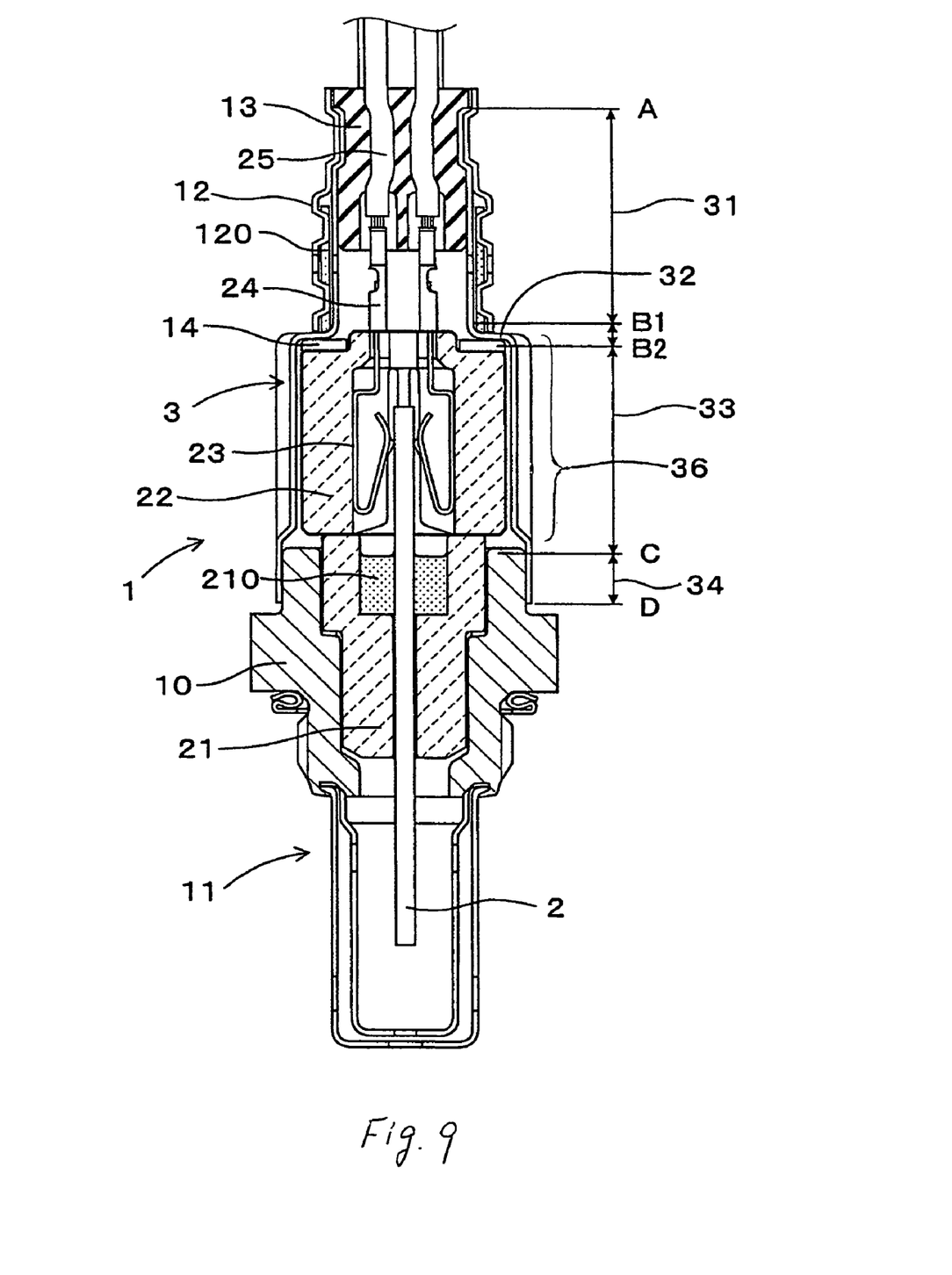
FIG. 9 is a longitudinal sectional view which shows a gas sensor according to the third embodiment of the invention.
Figure 10:
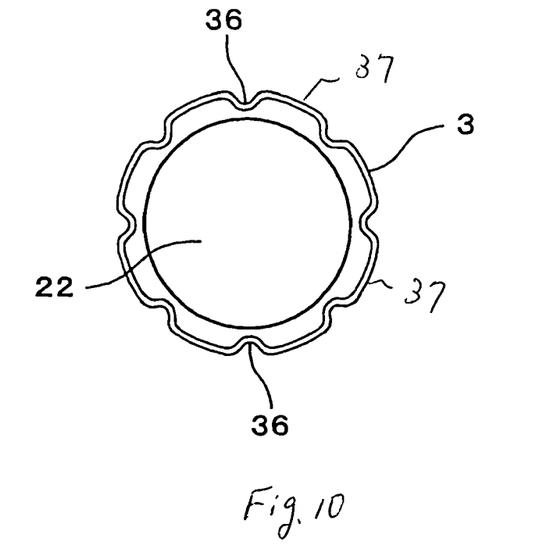
FIG. 10 is a transverse sectional view which shows an air cover and an upper porcelain insulator of the gas sensor, as illustrated in FIG. 9.
Figure 11:
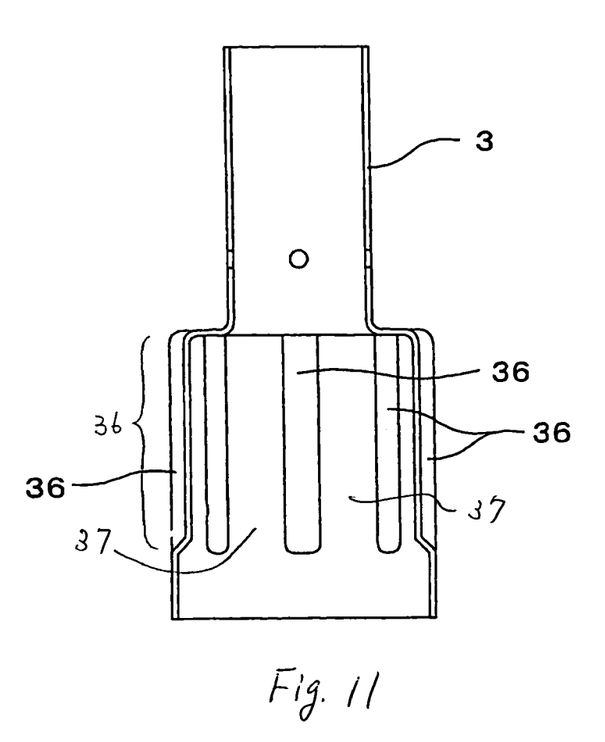
FIG. 11 is a longitudinal sectional view which shows an air cover of the gas sensor, as illustrated in FIG. 9.

FIGS. 9, 10, and 11 show the gas sensor 1 according to the third embodiment of the invention.

The gas sensor 1, like the one in FIG. 1, consists of the cylindrical housing 10, the sensor element 2 disposed within the housing 10 through the lower porcelain insulator 21, the protective cover assembly 11 installed in the top end of the housing 10, the cylindrical air cover 3 fitted on the base end of the housing 10, and the upper porcelain insulator 22 encompassing the base end portion of the sensor element 2 within the air cover 3.

The large-diameter portion 33 has, as clearly shown in FIGS. 10 and 11, a corrugated wall waving in a circumferential direction thereof to enhance the rigidity thereof. Specifically, the large-diameter portion 33 has recesses 36 and protrusions 37. Each of the recesses 36 is located between adjacent two of the protrusions 37 and formed by crimping the wall of the large-diameter portion 33 inwardly. The recesses 36 and the protrusions 37 extend in a longitudinal direction of the large-diameter portion 33 at regular intervals between the vicinity of the shoulder 32 and the lower end of the press-fit end 34.

The corrugated wall of the large-diameter portion 33 works as a rigidity enhancer to provide the rigidity to the air cover 3 which is sufficient to withstand mechanical deformation of the air cover 3 arising from physical impact acting thereon, thereby resulting in a decreased possibility of hit of the air cover 3 with the upper porcelain insulator 22 leading to cracks in the sensor element 2.

Figure 12:
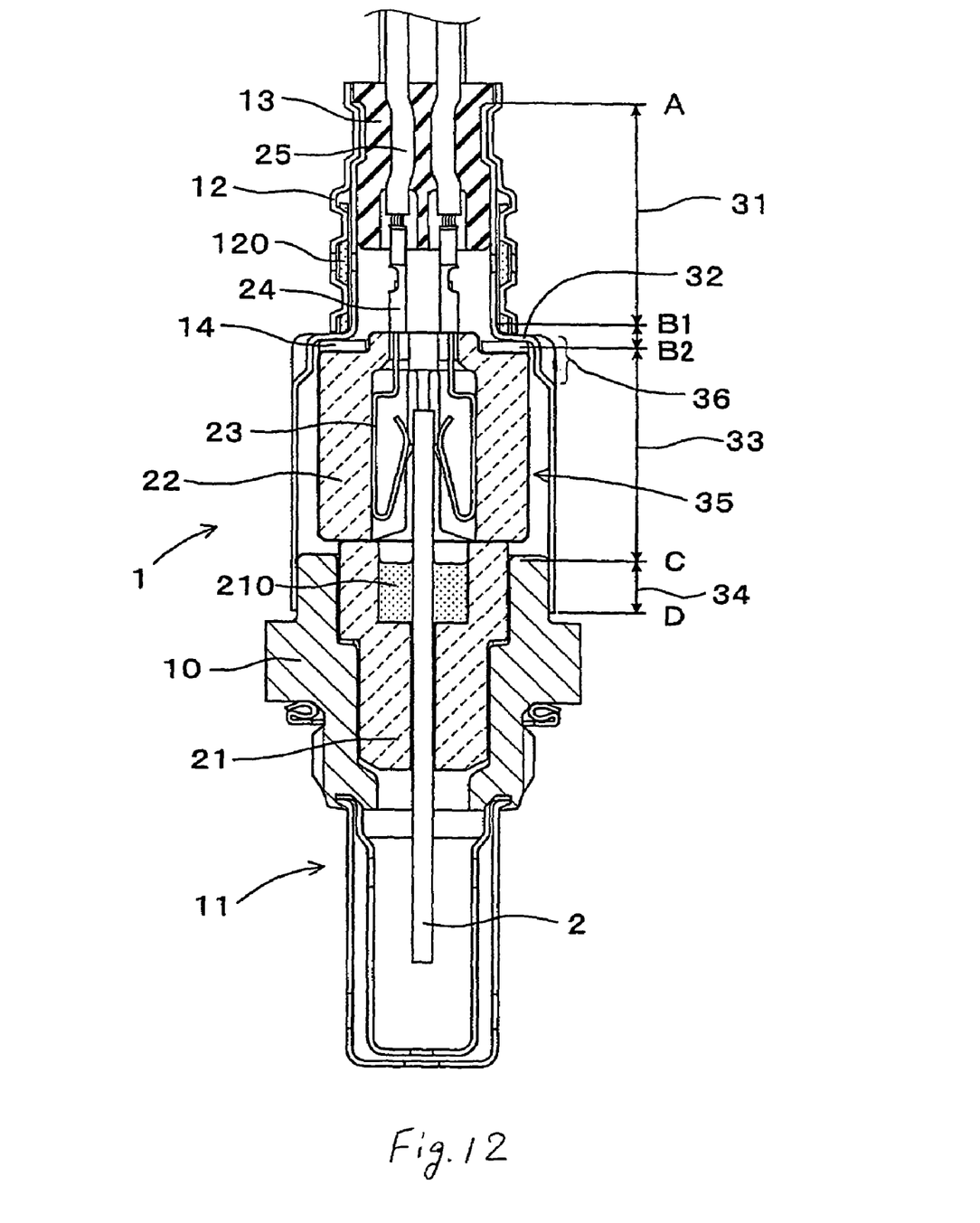
FIG. 12 is a longitudinal sectional view which shows a gas sensor according to the fourth embodiment of the invention.
Figure 13:
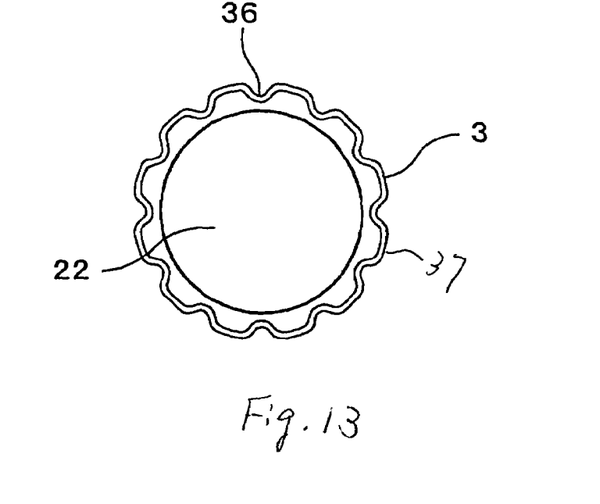
FIG. 13 is a transverse sectional view which shows an air cover and an upper porcelain insulator of the gas sensor, as illustrated in FIG. 12.
Figure 14:
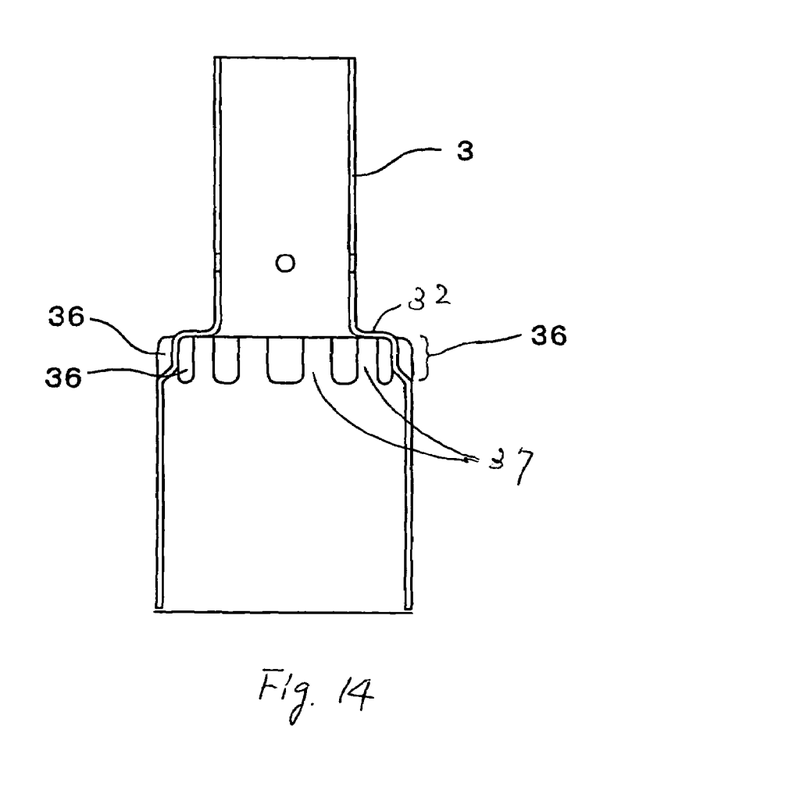
FIG. 14 is a longitudinal sectional view which shows an air cover of the gas sensor, as illustrated in FIG. 12.

FIGS. 12, 13, and 14 show the gas sensor 1 according to the fourth embodiment of the invention.

The gas sensor 1 has the recesses 36 in the air cover 3 and the buffer 35. The recesses 36, as clearly shown in FIG. 14, are formed only on an upper portion of the side wall the large-diameter portion leading to the shoulder 32. The buffer 35 is, as can be seen in FIG. 12, provided beneath the ridges 36. A portion of the large-diameter portion 33 facing the buffer 35 may have a Vickers hardness of 200 to 400. This structure also improves the rigidity of the large-diameter portion 33.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. For example, the gas sensor 1 may be designed to have a combination of some of the features, as described in the above embodiments, in order to avoid cracks in the sensor element 2.

What is claimed is:

1. A gas sensor comprising:
a hollow cylindrical housing having a top end portion and a base end portion;
a first porcelain insulator disposed in said housing;
a sensor element having a length made up of a sensing portion and a base portion, said sensor element being retained in said housing through said first porcelain insulator;
a cylindrical gas cover affixed to the top end portion of said housing to cover the sensing portion of said sensor element;
a second porcelain insulator in which the base portion of said sensing element is disposed;
a cylindrical air cover covering said second porcelain insulator, said air cover having a length made up of a small-diameter portion, a large-diameter portion, a shoulder formed between the small-diameter portion and the large-diameter portion, and a press-fit end continuing from the large-diameter portion, the small-diameter portion being crimped to retain an elastic insulator therein, the press-fit end being press fit on the base end portion of said housing to make a joint of said air cover to said housing, the large-diameter portion having an inner side wall facing an outer side wall of said second porcelain insulator; and
a buffer provided by a clearance between the inner side wall of the large-diameter portion of said air cover and the outer side wall of said second porcelain insulator, the clearance being in a range of 1 to 2.5 mm at a minimum.

2. A gas sensor as set forth in claim 1, wherein said buffer extends over a whole of the inner side wall of the large-diameter portion of said air cover in a lengthwise direction of said air cover.

3. A gas sensor as set forth in claim 1, wherein said air cover has a wall thickness of 0.3 to 0.8 mm.

4. A gas sensor as set forth in claim 1, wherein said air cover is made of an austenitic stainless steel.

5. A gas sensor comprising:
a hollow cylindrical housing having a top end portion and a base end portion;
a first porcelain insulator disposed in said housing;
a sensor element having a length made up of a sensing portion and a base portion, said sensor element being retained in said housing through said first porcelain insulator;
a cylindrical gas cover affixed to the top end portion of said housing to cover the sensing portion of said sensor element;
a second porcelain insulator in which the base portion of said sensing element is disposed; and
a cylindrical air cover covering said second porcelain insulator, said air cover having a harder portion whose Vickers hardness lies within a range of 200 to 400.

6. A gas sensor as set forth in claim 5, wherein said air cover has a length made up of a small-diameter portion, a large-diameter portion, a shoulder formed between the small-diameter portion and the large-diameter portion, and a press-fit end continuing from the large-diameter portion, the small-diameter portion being crimped to retain an elastic insulator therein, the large-diameter portion having an inner wall facing said second porcelain insulator, the press-fit end being press fit on the base end portion of said housing to make a joint of said air cover to said housing, the press-fit end having a Vickers hardness of 140 to 200.

7. A gas sensor as set forth in claim 5, wherein said air cover has a work-hardened surface.

8. A gas sensor as set forth in claim 5, wherein said air cover has a wall thickness of 0.3 to 0.8 mm.

9. A gas sensor as set forth in claim 5, wherein said air cover is made of an austenitic stainless steel.

10. A gas sensor comprising:
    a hollow cylindrical housing having a top end portion and a base end portion;
    a first porcelain insulator disposed in said housing;
    a sensor element having a length made up of a sensing portion and a base portion, said sensor element being retained in said housing through said first porcelain insulator;
    a cylindrical gas cover affixed to the top end portion of said housing to cover the sensing portion of said sensor element;
    a second porcelain insulator in which the base portion of said sensing element is disposed;
    a cylindrical air cover covering said second porcelain insulator; and
    a rigidity enhancer provided in said air cover which provides an increased rigidity to said air cover.

11. A gas sensor as set forth in claim 10, wherein said rigidity enhancer is implemented by protrusions and recesses each of which is disposed between adjacent two of the protrusions, the protrusions and recesses extending in an axial direction of the gas sensor.

12. A gas sensor as set forth in claim 10, wherein said air cover has a wall thickness of 0.3 to 0.8 mm.

13. A gas sensor as set forth in claim 10, wherein said air cover is made of an austenitic stainless steel.

* * * * *